United States Patent
Spencer et al.

(10) Patent No.: US 10,688,212 B2
(45) Date of Patent: Jun. 23, 2020

(54) FILTER-GASKET ASSEMBLY WITH SEAL AND PLACEMENT INDICATOR FOR STERILIZATION RIGID CONTAINER

(71) Applicant: O&M Halyard, Inc., Mechanicsville, VA (US)

(72) Inventors: Anthony S. Spencer, Woodstock, GA (US); Prasad S. Potnis, Johns Creek, GA (US); Christena K. Nash, Alpharetta, GA (US); Kun-Chi Wu, Johns Creek, GA (US); Brian E. Lin, Cumming, GA (US); Sharon S. Chang, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

(21) Appl. No.: 16/342,698

(22) PCT Filed: Jun. 28, 2018

(86) PCT No.: PCT/US2018/039930
§ 371 (c)(1),
(2) Date: Apr. 17, 2019

(87) PCT Pub. No.: WO2019/006079
PCT Pub. Date: Jan. 3, 2019

(65) Prior Publication Data
US 2020/0114032 A1    Apr. 16, 2020

Related U.S. Application Data

(60) Provisional application No. 62/527,193, filed on Jun. 30, 2017, provisional application No. 62/546,040, filed on Aug. 16, 2017.

(51) Int. Cl.
*A61L 2/26*        (2006.01)
*B65D 51/24*       (2006.01)
(Continued)

(52) U.S. Cl.
CPC ...... *A61L 2/26* (2013.01); *A61L 2/07* (2013.01); *A61L 2/14* (2013.01); *A61L 2/206* (2013.01);
(Continued)

(58) Field of Classification Search
CPC ...... A61L 2/07; A61L 2/14; A61L 2/26; A61L 2/206; B65D 51/248
See application file for complete search history.

(56) References Cited

U.S. PATENT DOCUMENTS 3,527,400 A    9/1970   Shepherd et al.
3,730,338 A    5/1973   Chesky
(Continued)

FOREIGN PATENT DOCUMENTS

WO    WO 2008/078169 A2    7/2008
WO    WO 2016/032853 A1    3/2016

OTHER PUBLICATIONS

International Search Report and Written Opinion for PCT/US2018/039930, dated Jan. 2, 2019, 19 pages.

*Primary Examiner* — Sean E Conley
(74) *Attorney, Agent, or Firm* — Dority & Manning, P.A.

(57) ABSTRACT

Sterilization packaging systems with features for sealing a volume against an ingress of contaminants are provided. Such features include a sealing assembly including a gasket and a sheet of filter material. The sealing assembly seals a lid to a seal rim of a base. The gasket has an upper surface, outer edge, and inner edge. The upper surface of the gasket comprises a first row of alternating protrusions and indentations and a second row of alternating protrusions and indentations that define a channel therebetween. The sheet of filter material extends from an inner edge of the gasket. The gasket completely surrounds the sheet of filter material, wherein the indentations and channel facilitate delivery of a sterilization agent through the filter material. A sterilization assembly including a lid having a plurality of protrusions in
(Continued)

its upper surface in conjunction with a gasket having a smooth upper surface is also provided.

17 Claims, 15 Drawing Sheets

(51) Int. Cl.
    *B65D 53/02* (2006.01)
    *B01D 46/10* (2006.01)
    *B01D 46/52* (2006.01)
    *A61L 2/07* (2006.01)
    *A61L 2/20* (2006.01)
    *A61L 2/14* (2006.01)
    *B65D 25/28* (2006.01)

(52) U.S. Cl.
    CPC ........... *B01D 46/10* (2013.01); *B01D 46/521* (2013.01); *B65D 25/2841* (2013.01); *B65D 51/248* (2013.01); *B65D 53/02* (2013.01); *A61L 2202/182* (2013.01); *A61L 2202/24* (2013.01)

(56) References Cited

U.S. PATENT DOCUMENTS

| | | |
|---|---|---|
| 4,193,496 A | 3/1980 | Barratt |
| 4,349,118 A | 9/1982 | Sanderson et al. |
| 4,466,552 A | 8/1984 | Butterworth et al. |
| 4,489,841 A | 12/1984 | Thompson |
| 4,551,311 A | 11/1985 | Lorenz |
| 4,643,303 A | 2/1987 | Arp et al. |
| 4,671,943 A | 6/1987 | Wahlquist |
| 4,706,839 A | 11/1987 | Spence |
| 4,774,063 A | 9/1988 | Runnells |
| 4,919,888 A | 4/1990 | Spence |
| 5,372,787 A | 12/1994 | Ritter |
| 5,407,069 A | 4/1995 | Schmieding et al. |
| 5,573,741 A | 11/1996 | Riley |
| 5,641,065 A | 6/1997 | Owens et al. |
| 5,887,745 A | 3/1999 | Wood |
| 6,099,812 A | 8/2000 | Allen et al. |
| 6,247,609 B1 | 6/2001 | Gabele et al. |
| 6,311,838 B1 | 11/2001 | Johnson et al. |
| 6,350,418 B1 | 2/2002 | Venderpool et al. |
| 6,589,477 B1 | 7/2003 | Frieze et al. |
| 6,893,158 B1 | 5/2005 | Tipp et al. |
| 8,418,872 B2 | 4/2013 | Smith |
| 8,435,445 B2 | 5/2013 | Kral |
| 8,623,289 B2 | 1/2014 | Cesa et al. |
| 8,763,839 B2 | 7/2014 | Sakairi |
| 8,815,174 B2 | 8/2014 | Bacik et al. |
| 9,028,147 B2 | 5/2015 | Schmal et al. |
| 9,125,727 B2 | 9/2015 | Dallafior |
| 9,610,126 B2 | 8/2017 | Griffin |
| 2009/0266818 A1 | 10/2009 | Sauvageau |
| 2010/0154353 A1 | 6/2010 | Cesa et al. |
| 2015/0327934 A1 | 11/2015 | Thomas et al. |
| 2016/0108566 A1 | 4/2016 | Tseng et al. |

FILTER-GASKET ASSEMBLY WITH SEAL AND PLACEMENT INDICATOR FOR STERILIZATION RIGID CONTAINER

RELATED APPLICATION

The present application s the national stage entry of International Patent Application No. PCT/US2018/039930 having a filing date of Jun. 28, 2018, which claims priority to U.S. Provisional Application Ser. No. 62/527,193, filed on Jun. 30, 2017 and U.S. Provisional Application Ser. No. 62/546,040, filed on Aug. 16, 2017, the contents of which are incorporated herein in their entirety by reference thereto.

FIELD OF THE INVENTION

The subject matter of the present disclosure relates generally to sterilization packaging and sterilization packaging systems.

BACKGROUND

Personnel in the Central Service Room (CSR) or the Sterile Processing Department (SPD) of hospitals are commonly charged with the responsibility of packaging surgical supplies into various types of sterilization packaging systems and sterilizing the systems to ensure that the sterility of the packaged contents is maintained from sterilization to the point of reuse. Several activities are involved in the task of preparing medical supplies (e.g., devices, accessories, components, etc.) that are contained in the sterilization packaging system for delivery to the operating room, cardiac catheterization lab, emergency room, labor and delivery room, intensive care unit, pediatric care unit, specialized burn care units, and other surgical or medical units.

Much of the surgical instruments and supplies used in the operating room are reusable. These supplies typically include such things as clamps, scalpel blade handles, retractors, forceps, scissors, surgeon's towels, basins, and the like. All of these supplies must be collected after each procedure, decontaminated, washed, placed in a sterilization packaging system, and sterilized before they can be used again in another procedure. The sterilization packaging systems used must be of the size and shape to accommodate the items to be sterilized, must be compatible with and withstand the physical conditions of the sterilization process, and must be capable of maintaining the sterility of their contents post-sterilization.

Typical means of sterilizing instruments include, among others, autoclaving with pre-vacuum and gravity steam, exposure to ethylene oxide gas, and exposure to hydrogen peroxide plasma or vaporized hydrogen peroxide. After the packaging system and its contents have been sterilized, the sterilization package system typically is stored until it is needed for a surgical or medical intervention procedure, at which time it is transported to the operating room, cardiac catheterization lab, emergency room, labor and delivery room, intensive care unit, pediatric care unit, specialized burn care units, or any other surgical or medical unit, or it can be stored in an environmentally controlled room until it is needed by the medical staff for utilization in a surgical or medical intervention procedure.

Common sterilization packaging systems include sealable pouches, sterilization wraps, and rigid containers. Although each of these systems has some advantage compared to other systems, each of these typical packaging systems also has drawbacks. As an example, using a sterilization wrap to package items to be sterilized in a certain prescribed manner will permit the entry of sterilizing vapor/gas or other medium to sterilize the contents of the wrapped package while denying the ingress of contaminants such as bacteria and other infection causing materials or their vehicles after sterilization. As such, sterilization wraps generally provide a consistent barrier against the ingress of contaminants. However, during storage and transfer to the operating room, the wrapped package may be handled several different times; each time the wrapped package is handled, there is a potential that the sterile nature of the package contents can be compromised, e.g., by a tear, cut, or other breach of the wrapping material, which can occur due to over handling or careless manipulation of the wrapped package.

As another example, sterilization containers—such as, e.g., a metal box and a rigid top or lid that closes the metal box—also can permit the entry of sterilizing medium while denying the ingress of contaminants after sterilization. Unlike sterilization wraps, rigid sterilization containers usually avoid tears, cuts, and the like that can compromise the sterilized contents of the container. However, typical rigid sterilization containers are complex packaging systems, including several parts that must be precisely assembled to prevent compromising the contents of the container after sterilization. Further, some parts of the sterilization container assembly are prone to warping, denting, and breakage, as well as mismatching, loss, and/or other damage. Additionally, the gasketing could experience viscoelastic changes over time due to thermo-mechanical or physical stress associated with repeated sterilization, disinfection, and/or mechanical washing. Thus, even if the parts of the container can be assembled, damaged or worn parts can prevent proper assembly or closure of the sterilization container and thereby allow the ingress of contaminants after sterilization.

In particular, the gasket that is used to seal the container lid to the container base is typically integrated into the container lid, which is reusable, where such reusability can lead to the formation defects in the gasket. For instance, over time the gasket can experience wear and tear, which results in a decrease in its compressibility and, as a result, its sealing performance. Further, deformations in the lid can cause the gasket to be move out of optimal placement with the base, creating a gap in the seal between the lid and the base. In addition, the number of sterilization cycles to which a gasket is subjected is not easily tracked and there is no indication for when a gasket needs to be replaced.

Moreover, considering the filter and gasket design specifically, in some designs, proper filter placement cannot be confirmed once the container is closed. In addition, most rigid containers have complicated assemblies where the filters and gaskets are held in place by retention plates with various locking mechanisms, which complicates the assembly and lead to variation in how a filter is sealed, which increases the risk for bacterial ingress. Furthermore, the gaskets and locking mechanisms for the retention plate can degrade over time, which can also increase the potential for bacterial ingress.

Consequently, there is a need for a sterilization packaging system that overcomes the shortcomings of known packaging systems. In particular, a sterilization packaging system that includes a one-time or known limited use filter and gasket assembly would be beneficial to avoid the risk of not having a proper seal that can occur when a gasket has been reused an unknown number of times. Additionally, a sterilization packaging system that indicates to the user that a proper seal between the lid and base has been achieved would be advantageous. Moreover, a sterilization packaging system that provides a continuous sealing interface, that eliminates the need for retention plates, and that eliminates multiple interfaces associated with the base, lid, gasket, and filter would also be useful.

SUMMARY

The present invention provides sterilization packaging systems with features for sealing a volume containing items to be sterilized against an ingress of contaminants. The sterilization packaging system includes a lid, a base, and a sealing assembly. The lid has an upper surface defining a perimeter and a lip extending downward from the perimeter, where the lip includes a plurality of upper openings and a plurality of lower openings. The base has a lower surface, a first sidewall, a second sidewall, a third sidewall, and a fourth side wall extending from the lower surface, where the first sidewall, the second sidewall, the third sidewall, and the fourth sidewall terminate at a seal rim defining a perimeter. The sealing assembly seals the lid to the seal rim of the base and includes a gasket and a sheet of filter material. The gasket has an upper surface, an outer edge, and an inner edge, where the upper surface of the gasket comprises a first row of alternating protrusions and indentations and a second row of alternating protrusions and indentations that define a channel therebetween. The sheet of filter material extends from an inner edge of the gasket, where the gasket completely surrounds and partially overlaps the sheet of filter material, where the indentations and channel facilitate the delivery of sterilization agent through the sheet of filter material when the sterilization packaging system is sealed with the sealing assembly.

In one particular embodiment, a visual indicator can be present on the outer edge of the gasket. Further, the visual indicator can be visible from the lower opening in the lip when the sterilization packaging system is adequately sealed by the sealing assembly. In addition, the visual indicator can protrude from the lower opening in the lip when the sterilization packaging system is adequately sealed by the sealing assembly.

In another embodiment, the seal rim can include an upper horizontal flange, where the upper surface of the gasket, the outer edge of the gasket, and the inner edge of the gasket define a recess for receiving the upper horizontal flange.

In yet another embodiment, the gasket can include a first gasket material and a second gasket material. Further, the first gasket material can be less compressible and more rigid (e.g., less conformable or deformable) than the second gasket material to avoid structural deformation and provide durability. In addition, the inner edge of the gasket can be defined by the first filter material. Moreover, the first gasket material can include a rigid polymer and the second gasket material can include a foam, which provides an improved seal between lid and base and even help to overcome slight deformations in the reusable portion of design caused by normal wear and tear.

In still another embodiment, the sheet of filter material can be corrugated to provide increased durability and prevent puncturing from packaged instruments and from external challenges during handling.

In one more embodiment, the sheet of filter material can extend in a longitudinal direction and a transverse direction, where one or more longitudinal support members can be disposed on a surface of the sheet of filter material in the longitudinal direction and one or more transverse support members can be disposed on the surface of the sheet of filter material in the transverse direction.

In an additional embodiment, the sealing assembly can provide a continuous sealing interface between the lid and the base of the sterilization packaging system.

Further, the sealing assembly can be disposable, while the lid and base can be reusable.

In still another embodiment, the gasket can include a pair of interior facing opposing tabs.

In one more embodiment, the seal rim can include an outer vertical flange and a lower horizontal flange, wherein an angle formed between the outer vertical flange and the lower horizontal flange ranges from about 65° to about 90°.

In an additional embodiment, the seal rim comprises an outer vertical flange and a lower horizontal flange, wherein the outer vertical flange includes a curved section having an area of compression that forms a point of tangency with the gasket.

The present invention also provides a sealing assembly for a sterilization packaging system. The sealing assembly includes a gasket comprising a first gasket material and a second gasket material, where the first gasket material is less compressible and more rigid (e.g., less conformable or deformable) than the second gasket material, further where an upper surface of the gasket comprises a first row of alternating protrusions and indentations and a second row of alternating protrusions and indentations that define a channel therebetween, and a sheet of filter material extending from an inner edge of the gasket, where the inner edge is defined by the first gasket material, where the gasket completely surrounds and partially overlaps the sheet of filter material, where the indentations and channel facilitate the delivery of sterilization agent through the sheet of filter material when the sterilization packaging system is sealed with the sealing assembly.

In one particular embodiment, a visual indicator can be present on an outer edge of the gasket, where the outer edge of the gasket is defined by the first gasket material.

In another embodiment, the sheet of filter material can be corrugated.

In one more embodiment, the sheet of filter material can extend in a longitudinal direction and a transverse direction, where one or more longitudinal support members can be disposed on a surface of the sheet of filter material in the longitudinal direction and one or more transverse support members can be disposed on the surface of the sheet of filter material in the transverse direction.

In still another embodiment, the sealing assembly can provide a continuous sealing interface between a lid and a base of the sterilization packaging system.

In yet another embodiment, the sealing assembly can be disposable.

In still another embodiment, the gasket can include a pair of interior facing opposing tabs.

In one more embodiment, the seal rim can include an outer vertical flange and a lower horizontal flange, wherein an angle formed between the outer vertical flange and the lower horizontal flange ranges from about 65° to about 90°.

In an additional embodiment, the seal rim comprises an outer vertical flange and a lower horizontal flange, wherein the outer vertical flange includes a curved section having an area of compression that forms a point of tangency with the gasket.

The present invention also provides a sterilization packaging system having a volume for containing items to be sterilized. The sterilization packaging system includes a lid, a base, and a sealing assembly. The sealing assembly includes an upper surface defining a perimeter and a lip extending downward from the perimeter, where the upper surface comprises a plurality of protrusions, and where the lip includes a plurality of upper openings and a plurality of lower openings. The base has a lower surface, a first sidewall, a second sidewall, a third sidewall, and a fourth side wall extending from the lower surface, where the first sidewall, the second sidewall, the third sidewall, and the fourth sidewall terminate at a seal rim defining a perimeter. The sealing assembly seals the lid to the seal rim of the base and includes a gasket and a sheet of filter material. The gasket has an upper surface, an outer edge, and an inner edge, where the upper surface of the gasket is smooth, and where the upper surface of the gasket and each of the plurality of protrusions on the upper surface of the lid define a channel therebetween. The sheet of filter material extends from an inner edge of the gasket, where the gasket completely surrounds and partially overlaps the sheet of filter material, where each channel defined by each of the plurality of protrusions and the upper surface of the gasket facilitates the delivery of sterilization agent through the sheet of filter material when the sterilization packaging system is sealed with the sealing assembly.

In one particular embodiment, a visual indicator can be present on the outer edge of the gasket. Further, the visual indicator can be visible from the lower opening in the lip when the sterilization packaging system is adequately sealed by the sealing assembly. In addition, the visual indicator can protrude from the lower opening in the lip when the sterilization packaging system is adequately sealed by the sealing assembly.

In another embodiment, the seal rim can include an upper horizontal flange, where the upper surface of the gasket, the outer edge of the gasket, and the inner edge of the gasket define a recess for receiving the upper horizontal flange.

In yet another embodiment, the gasket can include a first gasket material and a second gasket material. Further, the first gasket material can be less compressible and more rigid (e.g., less conformable or deformable) than the second gasket material to avoid structural deformation and provide durability. In addition, the inner edge of the gasket can be defined by the first filter material. Moreover, the first gasket material can include a rigid polymer and the second gasket material can include a foam, which provides an improved seal between lid and base and even help to overcome slight deformations in the reusable portion of design caused by normal wear and tear.

In still another embodiment, the sheet of filter material can be corrugated to provide increased durability and prevent puncturing from packaged instruments and from external challenges during handling.

In one more embodiment, the sheet of filter material can extend in a longitudinal direction and a transverse direction, where one or more longitudinal support members can be disposed on a surface of the sheet of filter material in the longitudinal direction and one or more transverse support members can be disposed on the surface of the sheet of filter material in the transverse direction.

In an additional embodiment, the sealing assembly can provide a continuous sealing interface between the lid and the base of the sterilization packaging system.

Further, the sealing assembly can be disposable, while the lid and base can be reusable.

In still another embodiment, the gasket can include a pair of interior facing opposing tabs.

In one more embodiment, the seal rim can include an outer vertical flange and a lower horizontal flange, wherein an angle formed between the outer vertical flange and the lower horizontal flange ranges from about 65° to about 90°.

In an additional embodiment, the seal rim comprises an outer vertical flange and a lower horizontal flange, wherein the outer vertical flange includes a curved section having an area of compression that forms a point of tangency with the gasket.

It should be appreciated that the sealing assembly may be further configured with any of the additional features as described herein.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
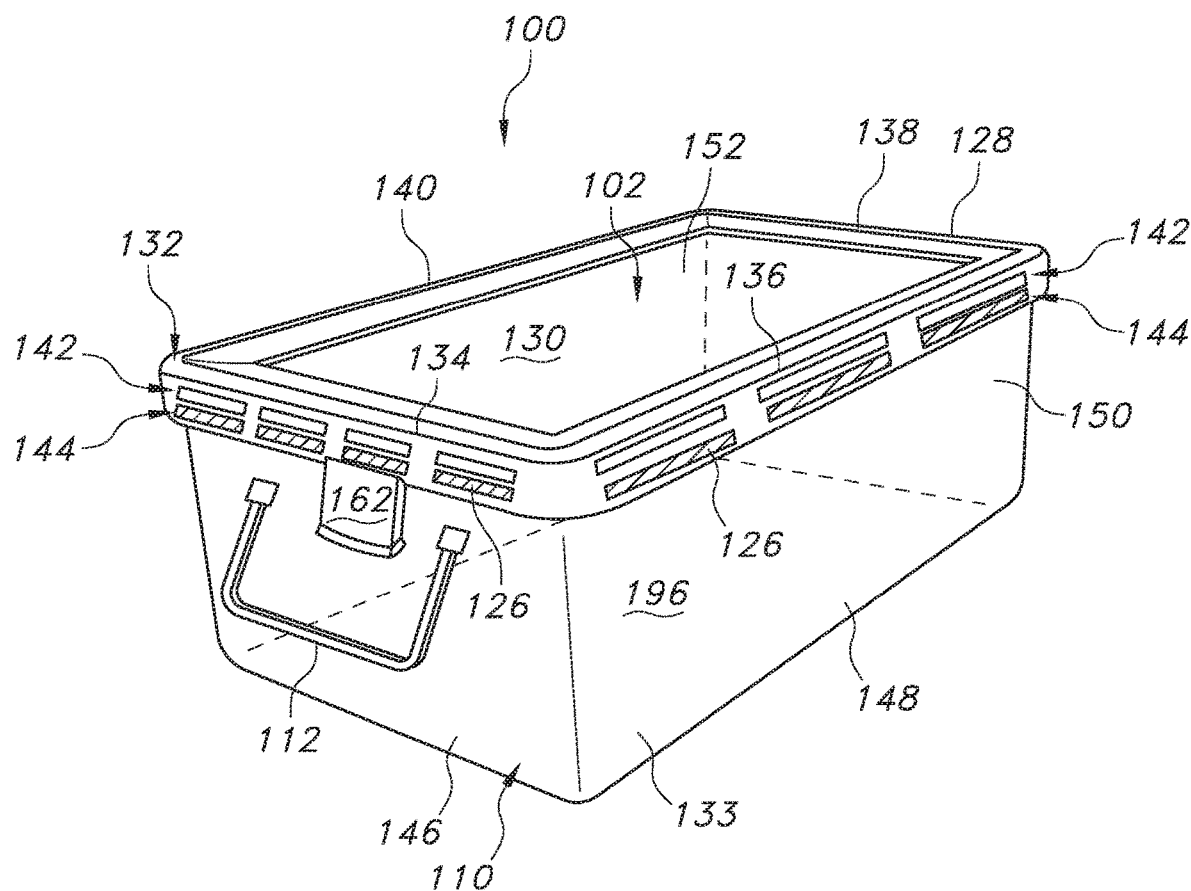
FIG. 1 provides a perspective view of a sterilization packaging system according to an exemplary embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein is a sterilization packaging system and components thereof suitable for use in a variety of procedures for containing, sterilizing, storing, and using sterilized items such as surgical supplies. While described in conjunction with its use in hospital and surgical room procedures, the present subject matter is intended for use wherever there is a need for sterilized materials. Consequently, the following description should not be considered a limitation as to the scope of use of the present subject matter.

Generally speaking, the present invention is directed to sterilization packaging systems with features for sealing a volume against an ingress of contaminants are provided. Such features include a sealing assembly that includes a gasket and a sheet of filter material, where the sealing assembly seals a lid to a seal rim of a base. The gasket has an upper surface, an outer edge, and an inner edge, wherein the upper surface of the gasket comprises a first row of alternating protrusions and indentations and a second row of alternating protrusions and indentations that define a channel therebetween. The sheet of filter material extends from an inner edge of the gasket, where the gasket completely surrounds the sheet of filter material, wherein the indentations and channel facilitate the delivery of sterilization agent through the sheet of filter material when the sterilization packaging system is sealed with the sealing assembly.

Figure 7:
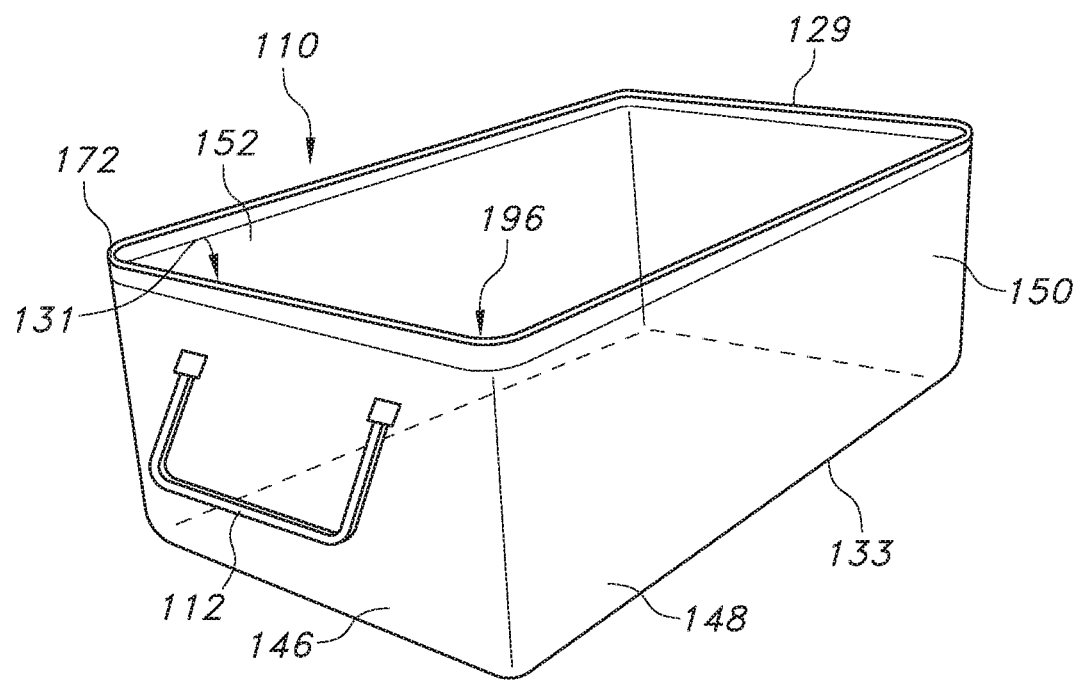
FIG. 7 provides a perspective view of the base of the sterilization packaging system of FIG. 1 according to an exemplary embodiment of the present invention.
Figure 8:
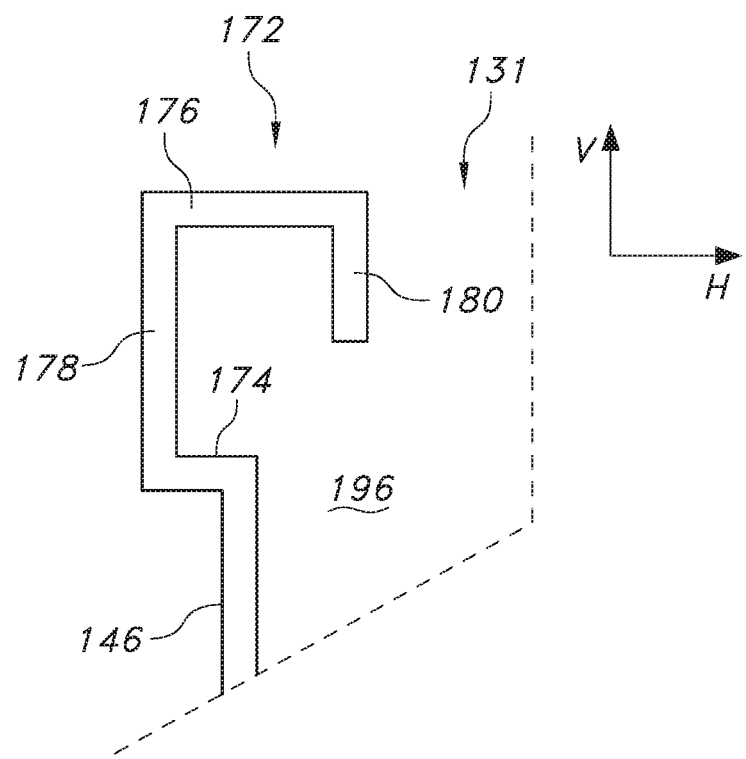
FIG. 8 provides a partial cross-section view of the base of the sterilization packaging system of FIG. 7.
Figure 9:
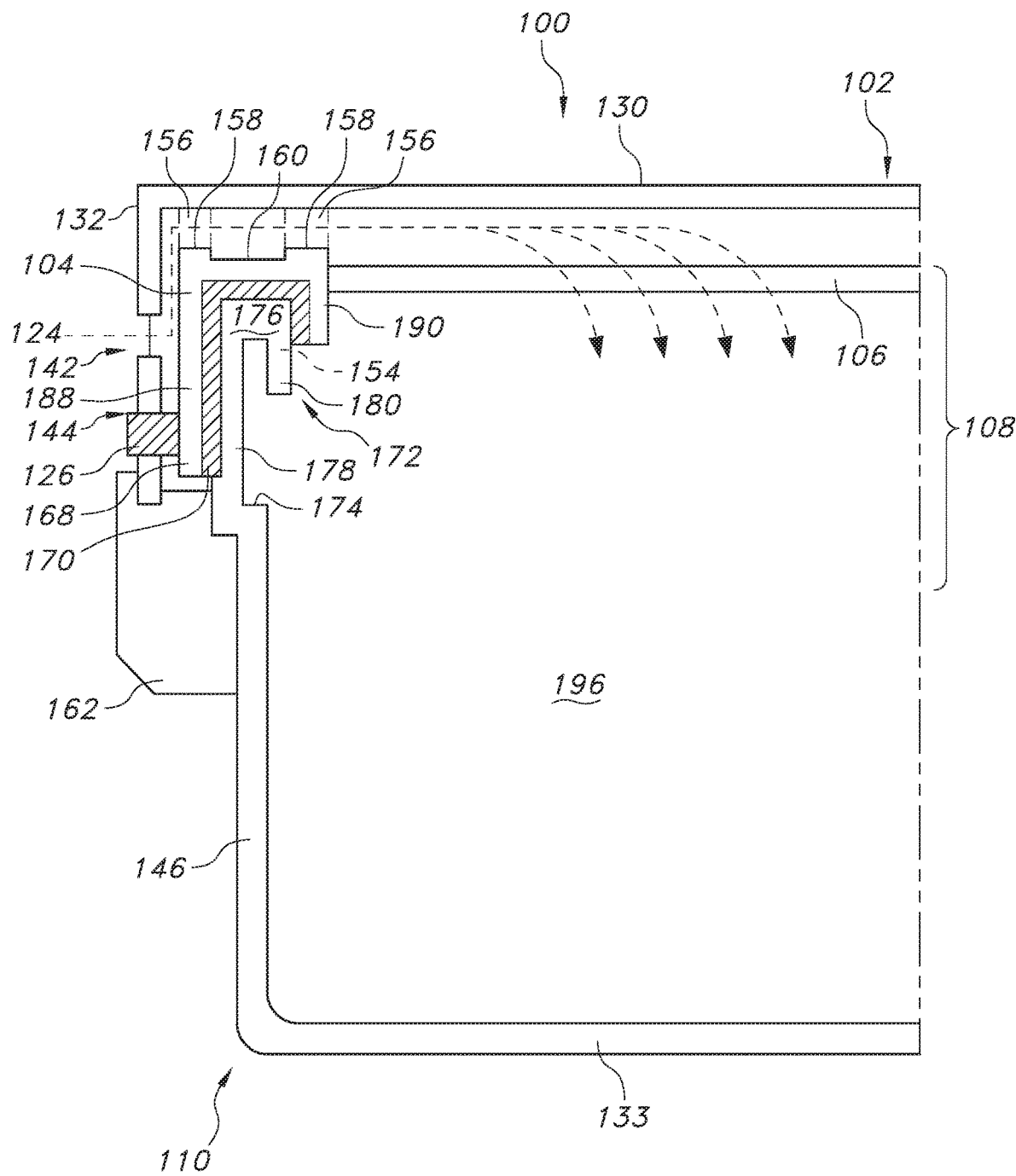
FIG. 9 provides a partial cross-section view of the sterilization packaging system when properly sealed by the sealing assembly according to an exemplary embodiment of the present invention.

FIG. 1 provides a perspective view of a sterilization packaging system according to an exemplary embodiment of the present subject matter. In the depicted embodiment, sterilization packaging system 100 includes a lid 102 and a base 110 defining a volume 196 for containing one or more items to be sterilized. The base 110 includes a lower surface 133, a first sidewall 146, a second sidewall 148, a third sidewall 150, and a fourth side wall 152 extending from the lower surface 133, where one or more handles 112 can be present on one or more of the sidewalls, although FIG. 1 shows a handle 112 present on the first sidewall 146. Referring to FIG. 7, which shows the base 110 without the lid 102 attached thereto, the first sidewall 146, the second sidewall 148, the third sidewall 150, and the fourth side wall 152 terminate at a seal rim 172 defining a perimeter 129. The various features of the seal rim 172 and how the seal rim 172 cooperates with the lid 102 to create a seal are shown in FIGS. 7 through 9 and will be discussed in more detail below. The base 110 also includes an opening 131 to provide access to the volume 196 in which items to be sterilized can be placed.

Referring again to FIG. 1, the lid 102 includes an upper surface 128 defining a perimeter 128, where a lip 132 extends downward therefrom towards the base 110. The lip 132 includes a plurality of upper openings 142 and a plurality of lower openings 144 that can be positioned along a first side 134, a second side 136, a third side 138, and a fourth side 140 of the lip. The upper openings 142 facilitate the introduction of any suitable type of sterilization agent (e.g., steam, ethylene oxide, or hydrogen peroxide plasma) into the opening 131 in the base 110 as discussed in more detail below. Meanwhile, the lower openings 144 can expose a visual indicator 126 when the lid 102 is adequately and properly sealed to the base 110 via a latch 162 that serves to engage and compress a sealing assembly between the lid 102 and the base 110. The base 110 and the lid 102 can be reusable and can be formed from a rigid material such stainless steel, anodized aluminum, polyetheretherketone (PEEK), polyaryletherketone, polyphenylsulphone (PPSU), polysulphone (PSU), filled PPSU, and filled PSU. Once sealed, the sealed sterilization packaging system 100 can then be transferred to sterilizing equipment and exposed to sterilization conditions as generally known in the art. Such sterilization conditions can include, for example, steam, ethylene oxide, or hydrogen peroxide plasma sterilization conditions. Sterilization conditions are the conditions present during a particular sterilization methodology utilized that substantially kills or completely destroys bacteria and other infectious organisms in an industrial or medical product to the desirable sterility assurance level (e.g., $\geq 10^{-6}$ log reduction for terminal sterilization).

Figure 2:
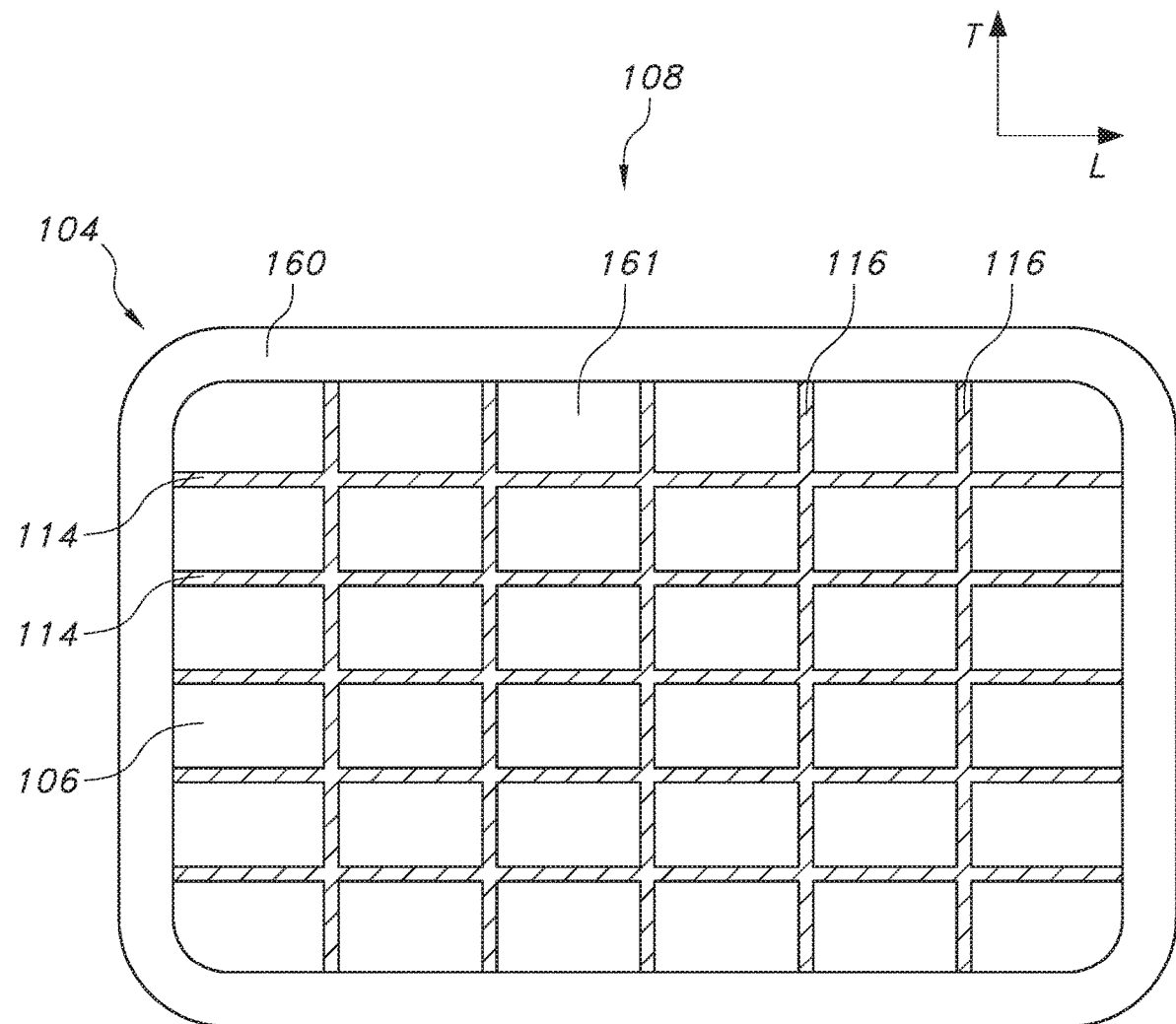
FIG. 2 provides a top view of a sealing assembly utilized in the sterilization packaging system of FIG. 1 according to an exemplary embodiment of the present invention.
Figure 3:
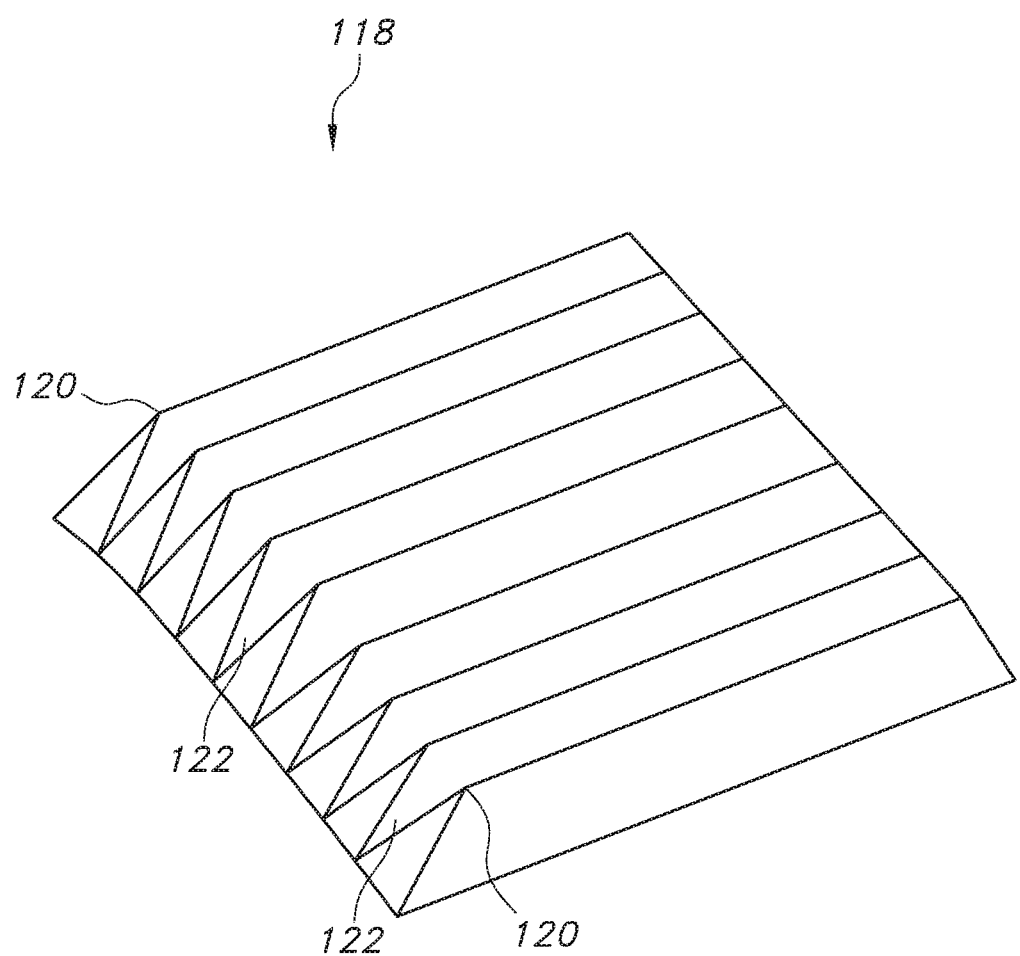
FIG. 3 provides a perspective view of a sheet of filter material utilized in the sealing assembly of FIG. 2 according to an exemplary embodiment of the present invention.
Figure 4:
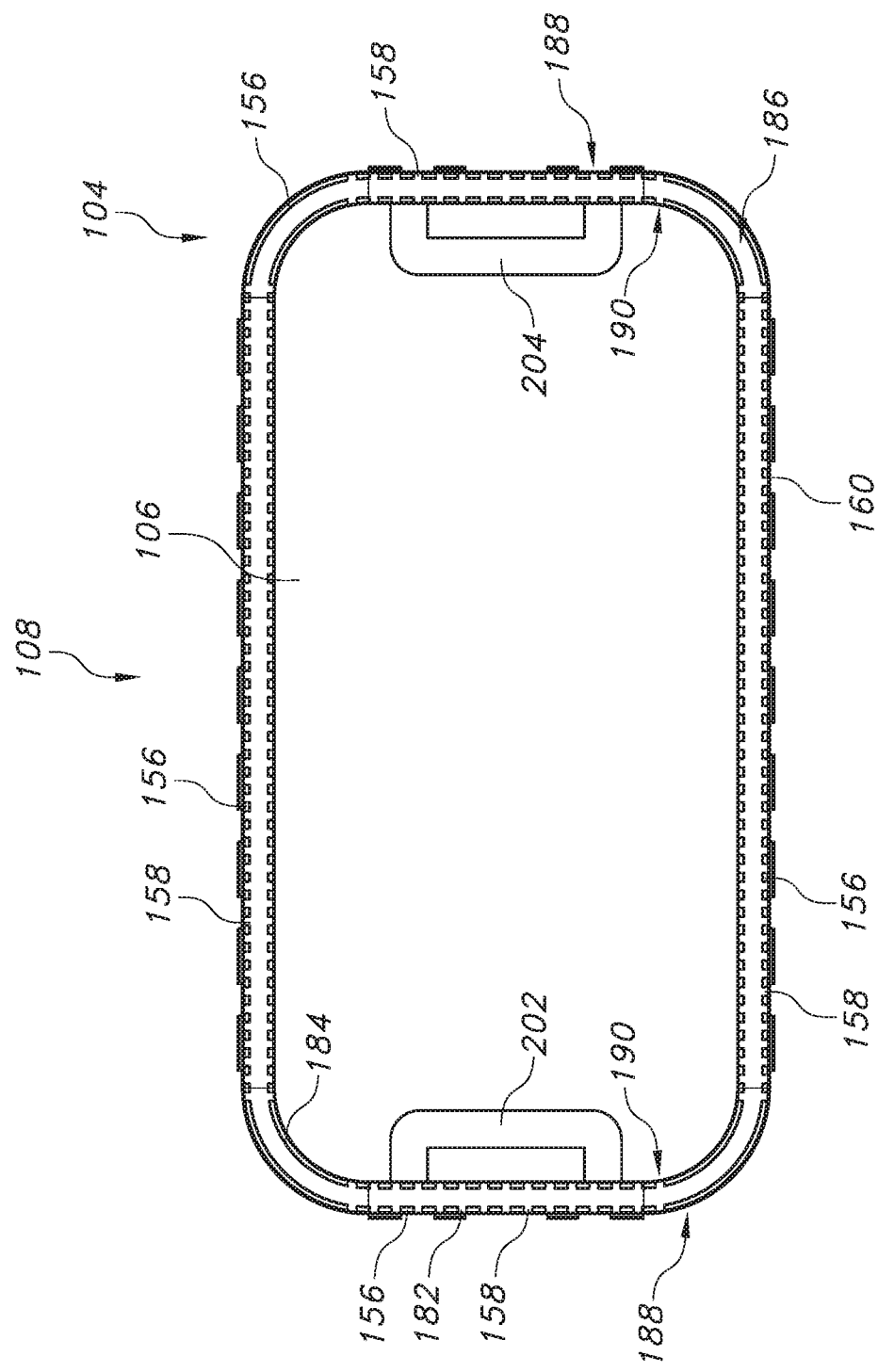
FIG. 4 provides a top view of a sealing assembly utilized in the sterilization packaging system of FIG. 1 according to an exemplary embodiment of the present invention, showing the rows of alternating protrusions and indentations present on a gasket according to an exemplary embodiment of the present invention.

Specifically and referring now to FIGS. 2 through 6, the lid 102 is sealed to the base 110 via a one-piece sealing assembly 108 that is engaged and compressed via latch 162. The sealing assembly 108 can be disposable and seals the base 110 from the ingress of contaminants such as, e.g., bacteria and other infection causing materials or their vehicles. As shown in FIGS. 2 and 4, the sealing assembly 108 includes a gasket 104 and a sheet of filter material 106. The gasket 104 completely surrounds the sheet of filter material 106.

The sheet of filter material 106 can be made from a number of materials and, generally, may be disposable in that the sheet of filter material 106 can be a one-use item that is discarded or recycled after their initial use. Generally, disposable materials can include nonwoven materials made from either or both natural and synthetic fibers such as paper, fibrous polymeric nonwovens, and films (e.g., PTFE porous films or membranes), which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant sheet of filter material 106 must be compatible with the particular sterilization technique being used and must also provide both strength and barrier properties to maintain the sterile nature of the contents of the sterilization package system 100 until use. In the illustrated exemplary embodiment, shown in FIGS. 2 through 6, the sheet of filter material 106 can be a transparent breathable film, a translucent or opaque material, such as, e.g., a translucent breathable film, a SMS material (described below), or the like.

For example, the sheet of filter material 106 may be a spunbonded-meltblown-spunbonded material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers that is also commonly referred to by the acronym "SMS." The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, the sheet of filter material 106 can be made from a SMS material, but it is to be understood that the sheet of filter material 106 also may be made from other suitable materials.

In one particular embodiment, as shown in FIG. 2, structural support can be provided to the sheet of filter material 106 in the form of a plurality of longitudinal support members 114 extending in a longitudinal direction L and a plurality of transverse support members 116 extending in a transverse direction T disposed on a upper surface 161 of the sheet of filter material 106, although it is to be understood that, alternatively, the longitudinal support members 114 and/or the transverse support members 116 can be disposed on a lower surface (not shown) of the sheet of filter material 106. Such an arrangement can provide the sheet of filter material 106 with improved structural durability. In addition, it is to be understood that the structural support can take any suitable shape or form and is not limited to the longitudinal support members 114 and transverse support members 116 shown in FIG. 2. For instance, the structural support can be in the form of a metal mesh or grid that is incorporated into the sheet of filter material 106 itself.

In still another embodiment and referring to FIG. 3, the filter component of the sealing assembly 108 can be a corrugated sheet of filter material 118. As shown, the corrugated sheet of filter material 118 includes a plurality of peaks 120 and valleys 122, where such a geometry can increase filtration efficiency and provide increased structural robustness to the filter component of the sealing assembly 108.

Figure 5:
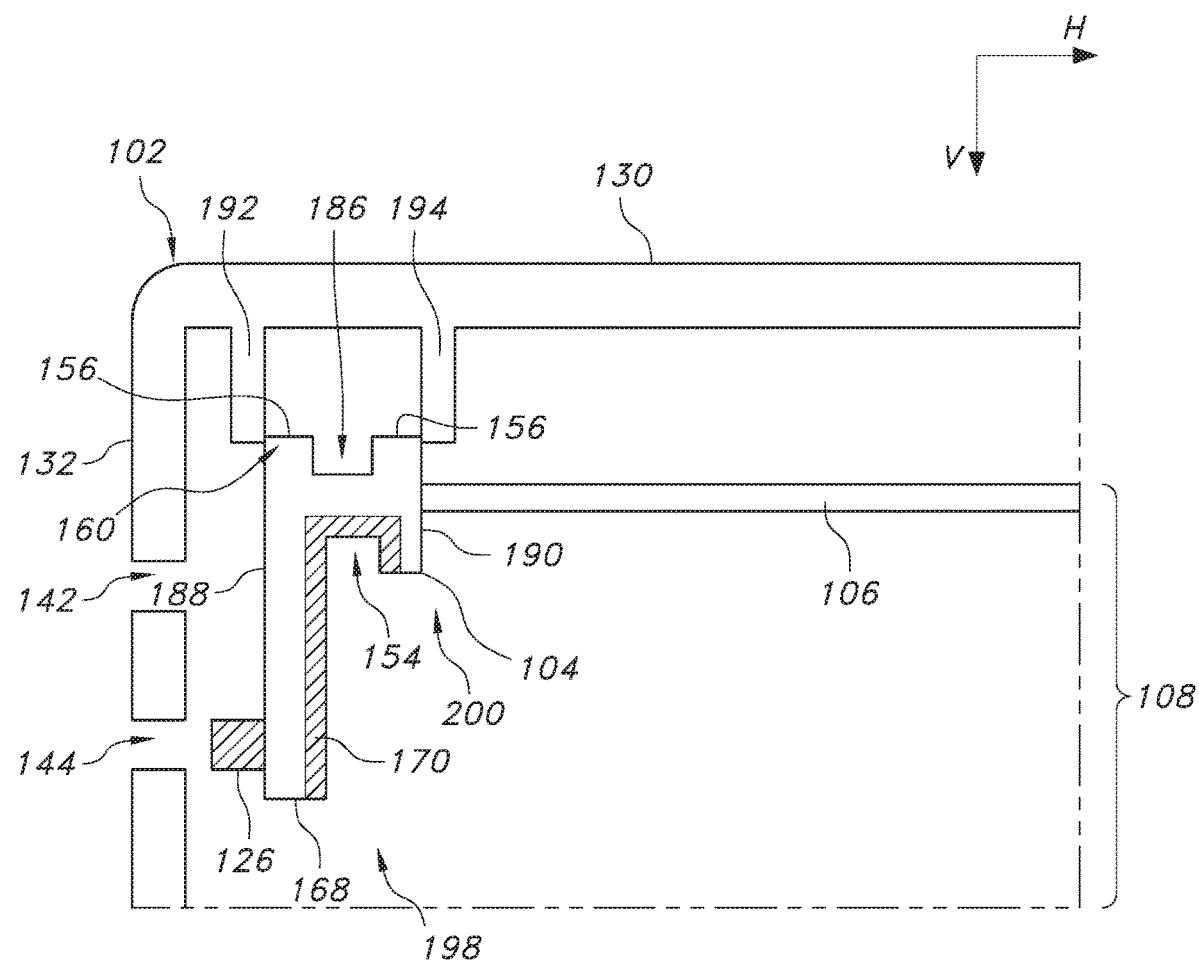
FIG. 5 provides a partial cross-section view of an exploded view of the sterilization packing system of FIG. 1, including the lid and sealing assembly, according to an exemplary embodiment of the present invention.
Figure 6:
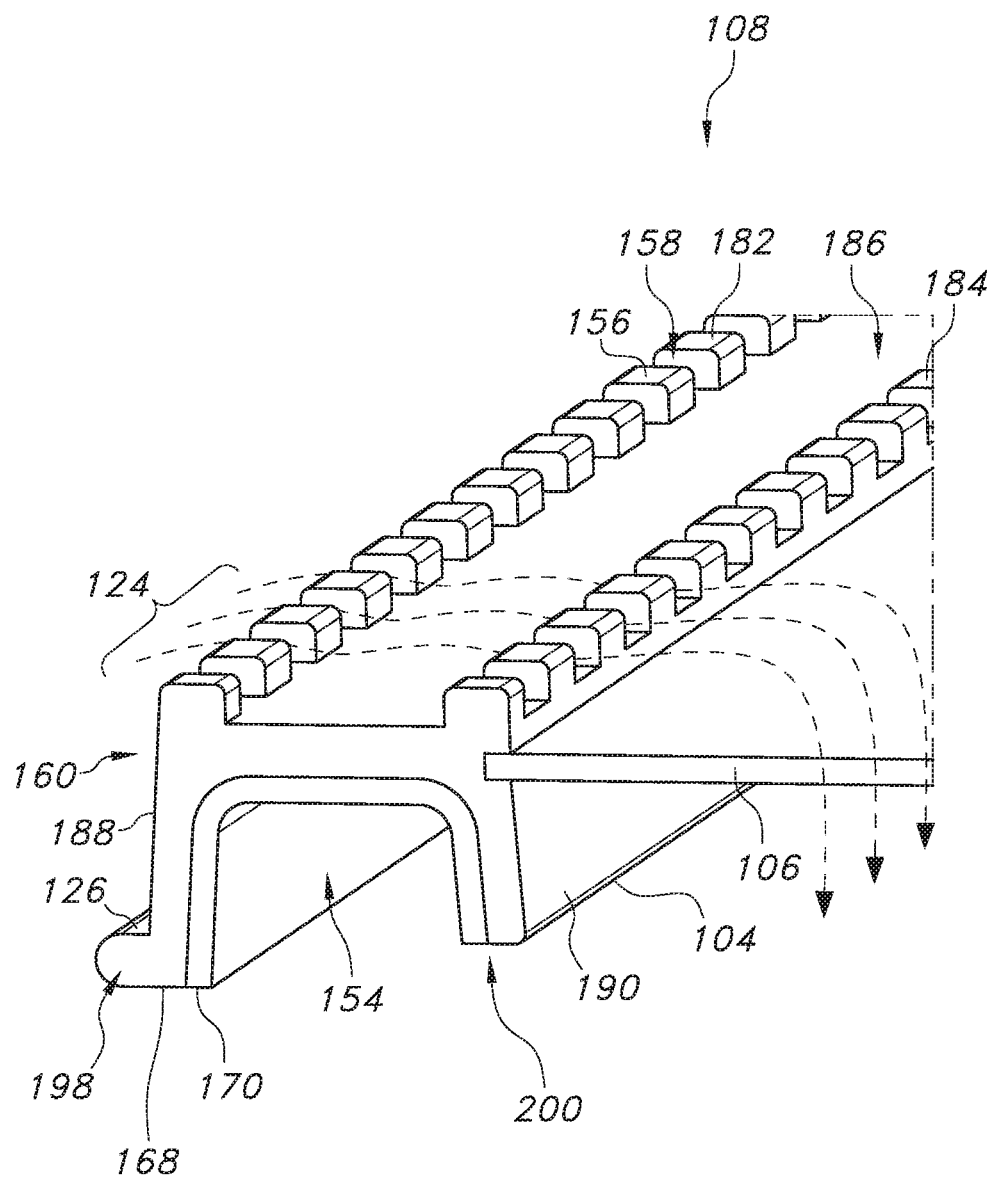
FIG. 6 provides a perspective view of the sealing assembly utilized in the sterilization packaging system of FIG. 1 according to an exemplary embodiment of the present invention.

Referring now to FIGS. 4 through 6, various features of the gasket 104 of the sealing assembly 108 are shown. Specifically, the gasket 104 completely surrounds the sheet of filter material 106 and provides a continuous sealing interface between the lid 102 and base 110 of the sterilization packaging system 100. The gasket 104 includes a plurality of protrusions 156 and indentations 158 on its upper surface 160 in a first row 182 adjacent an outer edge 188 of the gasket 104 and a second row 184 adjacent an inner edge 190 of the gasket 104 to define a channel 186 therebetween. The indentations 158 and channel 186 facilitate the delivery of sterilization agent 124 (e.g., steam, ethylene oxide, hydrogen peroxide plasma, etc.) into the base 110 of the sterilization packaging system via the sheet of filter material 106 to sterilize the contents contained within the volume 196 of the base 110. In addition, as shown in FIG. 4, the gasket 104 can include a pair of interior-facing, opposing tabs 202 and 204. The tabs 202 and 204 facilitate aseptic removal of the sealing assembly 108 once the lid 102 is removed to expose the sterilized contents contained within the packaging system 100 in the operating room, cardiac catheterization lab, emergency room, labor and delivery room, intensive care unit, pediatric care unit, specialized burn care units, or any other surgical or medical unit.

Referring to FIGS. 5 and 6, the sheet of filter material 106 extends from the inner edge 190 of the gasket 108 in a horizontal direction H. Further, in addition to the upper surface 160 of the gasket 108 with its plurality of protrusions 156 and indentations 158 described above, the gasket 108 also includes a first side portion 198 extending downward from the upper surface 160 in a vertical direction V and a second side portion 200 extending from the upper surface 160 in the vertical direction V. The upper surface 160, first side portion 198, and second side portion 200 define a recess 154 that receives the base 110 when sealing the lid 102 against the base 110. In some embodiments, it is to be understood that the lid 102 can include a first guide rail 192 and/or a second guide rail 194 to facilitate the proper placement of the lid 102 above the gasket 104, although the guide rails should be positioned in such a manner so as to allow the sterilization agent 124 to have a path by which it can still reach the sheet of filter media 106 from the indentations 158 and channel 186 in the gasket 104.

Moreover, although the gasket 104 can be formed from a single material, such as polyurethane, silicone, polyvulcanate, polyvinylidene chloride (PVDC), polytetrafluoroethylene (PTFE), polysulphones, a crosslinked elastomers, etc., in some embodiments, the gasket 104 can include a first gasket material 168 and a second gasket material 170, where the first gasket material 168 is more rigid and less compressible than the second gasket material 170. As such, the first gasket material 168 can provide structural support to the sheet of filter material 106, as the sheet of filter material 106 extends from the inner edge 190 of the gasket 104, which is defined by the first gasket material 168 as shown in FIGS. 5 and 6. For example, the first gasket material 168 can be formed from a rigid polymer such as non-foamed polyurethane, silicone, polyvulcanate, polyvinyl chloride (PVC), polyvinylidene chloride (PVDC), polyvinylidene fluoride (PVDF), polytetrafluorethylene (PTFE), crosslinked and mineral filled elastomers, and other hard durometer materials, while the second gasket material 170 can be formed from a more compressible material such as a foam, including foamed polyurethane, foamed silicones, foamed polyvinyl chloride (PVC), foamed elastomers, foamed polyvinylidene chloride (PVDC), polyvinylidene chloride (PVDF), and other soft durometer polymers, which can be located beneath the upper surface 160 of the gasket 104 and on the sections of the first side portion 198 of the gasket 104, the second side portion 200 of the gasket 104 that define the recess 154 so that the gasket 104 is sufficiently compressible to adequately seal the lid 102 to the base 110 at the seal rim 172. In one particular embodiment, the first gasket material 168 and the second gasket material 170 can be formed from the same base material but with different compression properties. For example, the first gasket material 168 and the second gasket material 170 can be the same polymer with two different durometers, where second gasket material 170, which is the material closer to the interface with the seal rim 172, has a lower durometer.

In addition, the gasket 104 can include a visual indicator 126 that can be present on the outer edge 188 of the gasket. As the gasket 104 is compressed to create a seal between the lid 102 and the base 110 of the sterilization packaging system 100, such as via the latch 162, the visual indicator 126, which can have a different color, texture, or a combination thereof, than the rest of the gasket 104, can be visible from the lower openings 144 in the lip 132 of the lid 102 to signal to a viewer that the sterilization packaging system 100 is sufficiently sealed to protect against the ingress of contaminants. In certain embodiments, such as that shown in FIG. 9, the gasket 104 can be designed such that the visual indicator 126 can protrude through the lower openings 144 in the lip 132 of the lid 102 when the sterilization packaging system 100 is sufficiently sealed.

Further, although the gasket 104 can be disposable to eliminate the risk of wear and tear on the gasket, which can result in inadequate sealing capabilities, in some embodiments, the gasket 104 can be formed from a reusable material that is more durable, such as elastomeric silicone, polytetrafluoroethylene, polyvinylidene fluoride, polyurethane, a polyolefin (e.g., polyethylene or polypropylene) that can withstand multiple sterilization cycles without losing their compressibility.

Turning now to FIGS. 7 and 8, the seal rim 172 of the base 110 of the sterilization packaging system 100 is discussed in more detail. As mentioned above, the first side wall 146, the second side wall 148, and third side wall 150 and the fourth side wall 152 of the base 110 terminate at seal rim 172. A cross-sectional view of the seal rim 172 at first side wall 146 is shown in FIG. 8 for illustrative purposes. The side wall 146 terminates at a lower horizontal flange 174 of the seal rim 172, which extends away from the opening 131 defined by the base 110 in the horizontal direction H. Further, an outer vertical flange 178 extends from the lower horizontal flange 174 in the vertical direction V, and an upper horizontal flange 176 then extends from the outer vertical flange 178 towards the opening 131 in the base 110. An inner vertical flange 180 then extends downward from the upper horizontal flange 176 in the vertical direction, where the outer vertical flange 178, the upper vertical flange 176, and the inner vertical flange 180 define a geometry that corresponds with the shape of the recess 154 in the gasket 104, as shown in FIG. 9.

Referring now to FIG. 9, a cross-sectional view of the sterilization packaging system 100 in its sealed state and taken at the location of the indentations 158 in the gasket 104 is described. As shown, the one-piece sealing assembly 108 including the gasket 104 and the sheet of filter material 106 extending from an inner edge 190 therefrom seals the lid 102 to the base 110 when the latch 162 is locked into place between the lid 102 and the base 110, resulting in compression of the gasket 104 against and around the seal rim 172. Further, to indicate to a viewer that the sterilization packaging system 100 is adequately sealed, a visual indicator 126 can be visible from and/or can protrude from the lower opening 144 in the lip 132 of the lid 102. Meanwhile, sterilization agent 124 can flow from the environment through the upper opening 142 in the lip, pass over the indentations 158 and channel 186 in the upper surface 160 of the gasket, and across the gasket 104 to the sheet of filter material 106, where the sterilization agent 124 can then penetrate into the volume 196 of contents to be sterilized located in the base 110. Further, the indentations 158 and channel 186 also allow for the possibility of a solid lid that is free from any perforations, which better protects the filter material 106. Further, the shape, size, and placement of the indentations 158 and channel 186 can be optimized to achieve the correct vent to volume ratio across the various sterilization modalities. In addition, the protrusions 158, which are shown in dashed lines, are in contact with the upper surface 130 of the lid 102 as the lid 102 is moved downward and secured to the base 110 by the latch 162. In the opposite direction, the upper horizontal flange 176, the outer vertical flange 178, and the inner vertical flange 180 fit into the recess 154 in the gasket 104 as the gasket 104 compresses and forms a seal around the seal rim 172. As a result of such an arrangement, a continuous, one-piece sealing interface is created between the lid 102 and the base 110, which eliminates the need for multiple seal interfaces, while also indicating to the user that a proper seal has been achieved to confirm that the sterilization packaging system 100 is indeed closed.

Figure 10:
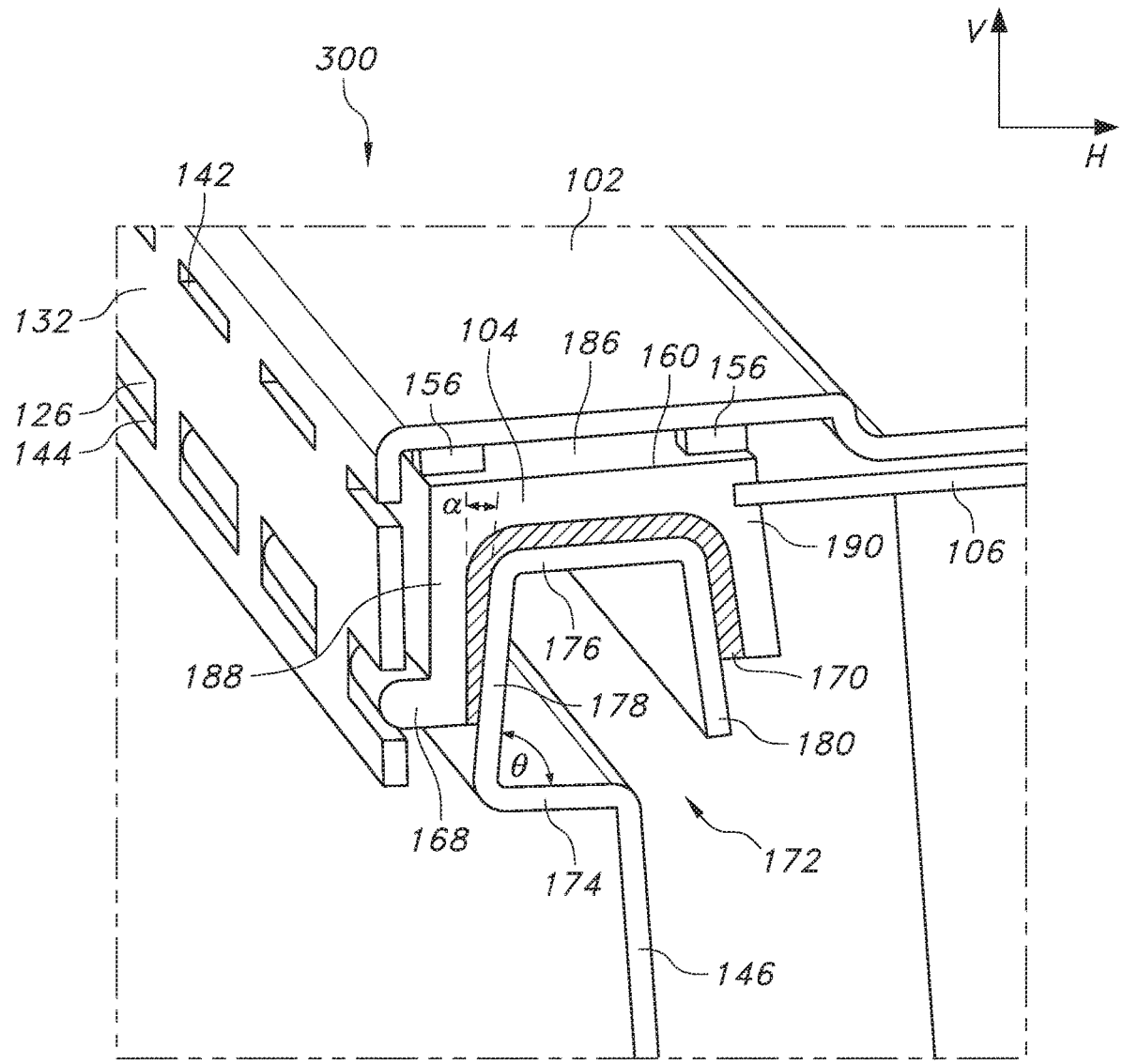
FIG. 10 provides a partial cross-section view of a sterilization packaging system according to another exemplary embodiment of the present invention.

Referring now to FIG. 10, a partial cross-section view of a sterilization packaging system according to another exemplary embodiment of the present invention is shown. Specifically, the seal rim 172 contains certain geometry to ensure that the visual indicator 126 can protrude through the lower opening 144 in the lip 132 of the lid 102 when the one-piece sealing assembly 108 is adequately sealed and correctly installed. For instance, an angle θ can be formed between the outer vertical flange 178 that extends in the vertical direction V and the lower horizontal flange 174 that extends in the horizontal direction that is offset slightly from the vertical direction or axis V. For instance, the angle formed between the outer vertical flange 178 and the lower horizontal flange can range from about 65° to about 90°, such as from about 70° to about 85°, such as from about 75° to about 80°. Likewise, the angle α formed between the outer edge 188 of the gasket 104 and the outer vertical flange 178 can range from about 0° to about 25° C., Such as from about 5° to about 20°, such as from about 10° to about 15°, where the deflection movement of the gasket 104 including the indicator 126 relative to the outer vertical flange 178 facilitates the indicator 126 to protrude from the lower opening 144. In this manner, the position of the outer vertical flange 178 encourages the compression of an optional second gasket material 170 and the proper placement of the outer edge 188 of the gasket 104 so that the visual indicator 126 can protrude through the lower openings 144 in the lip 132 of the lid 102, which signals to the user that the gasket 102 is properly sealed between the seal rim 172 and the lid 102.

Figure 11A:
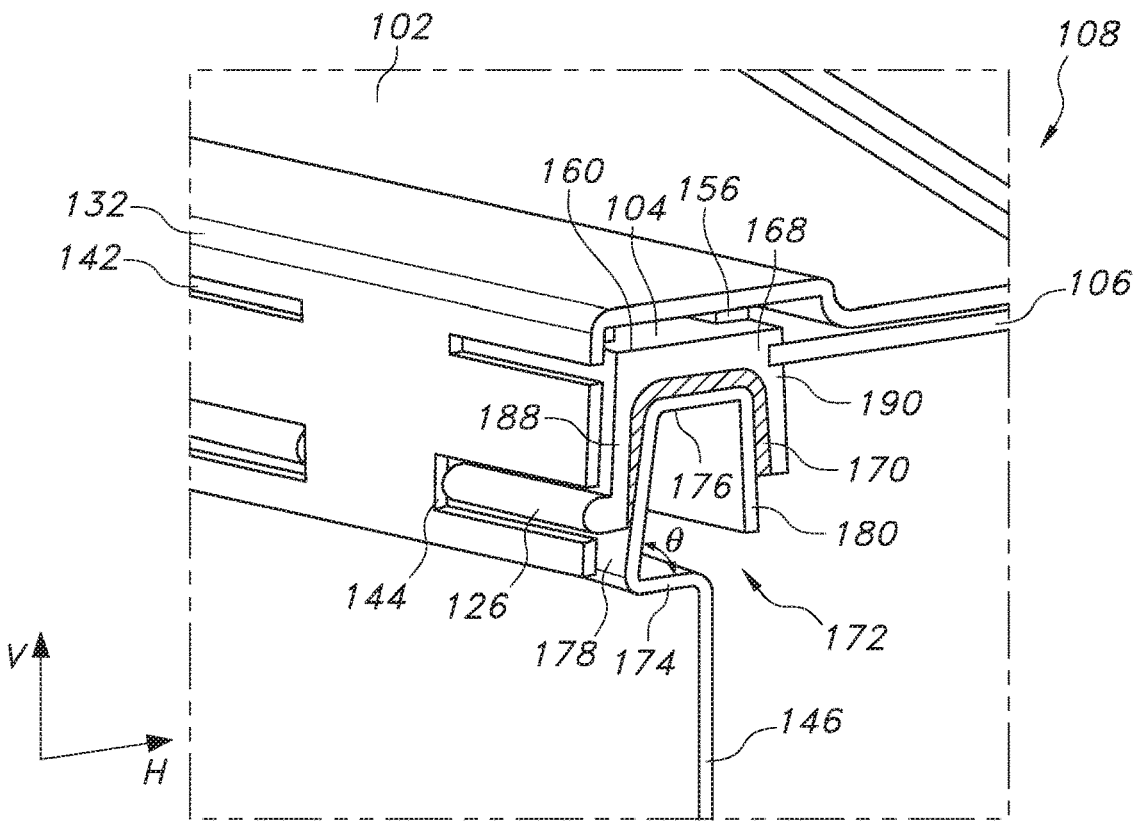
FIG. 11A provides another partial cross-section view of the sterilization packaging system of FIG. 10 when the sealing assembly is properly installed.
Figure 11B:
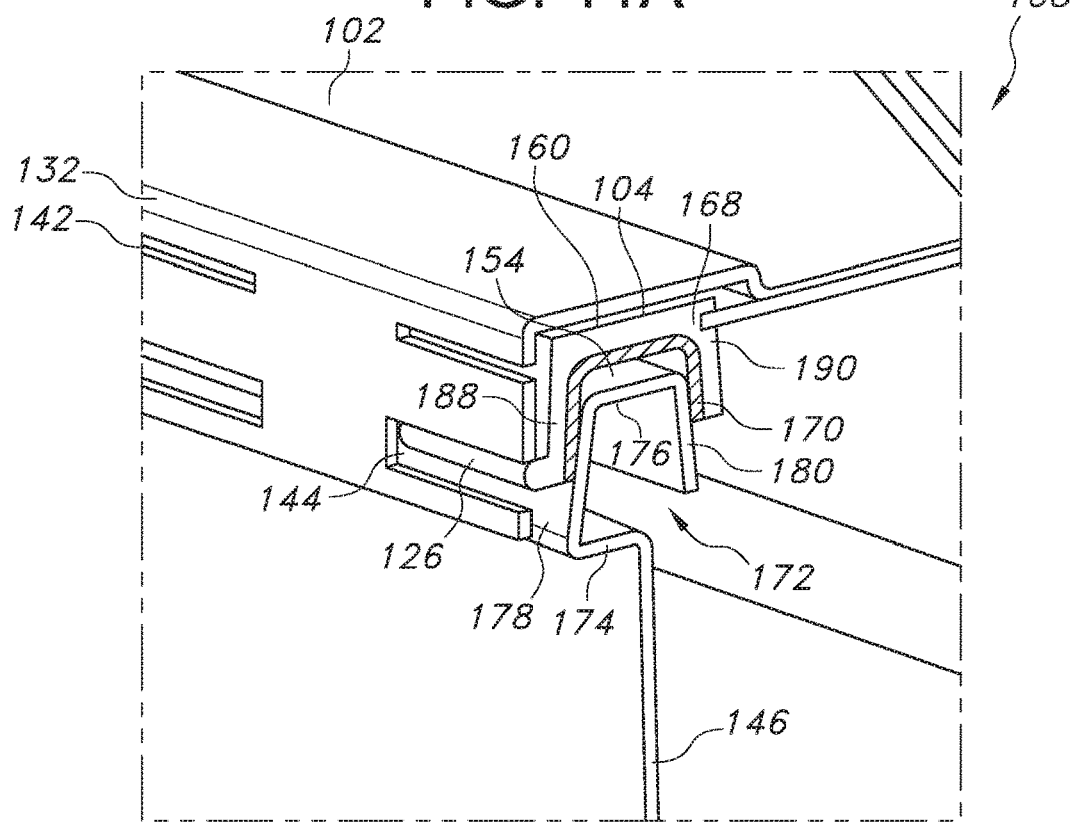
FIG. 11B provides another partial cross-section view of the sterilization packaging system of FIG. 10 when the sealing assembly is improperly installed.
Figure 11C:
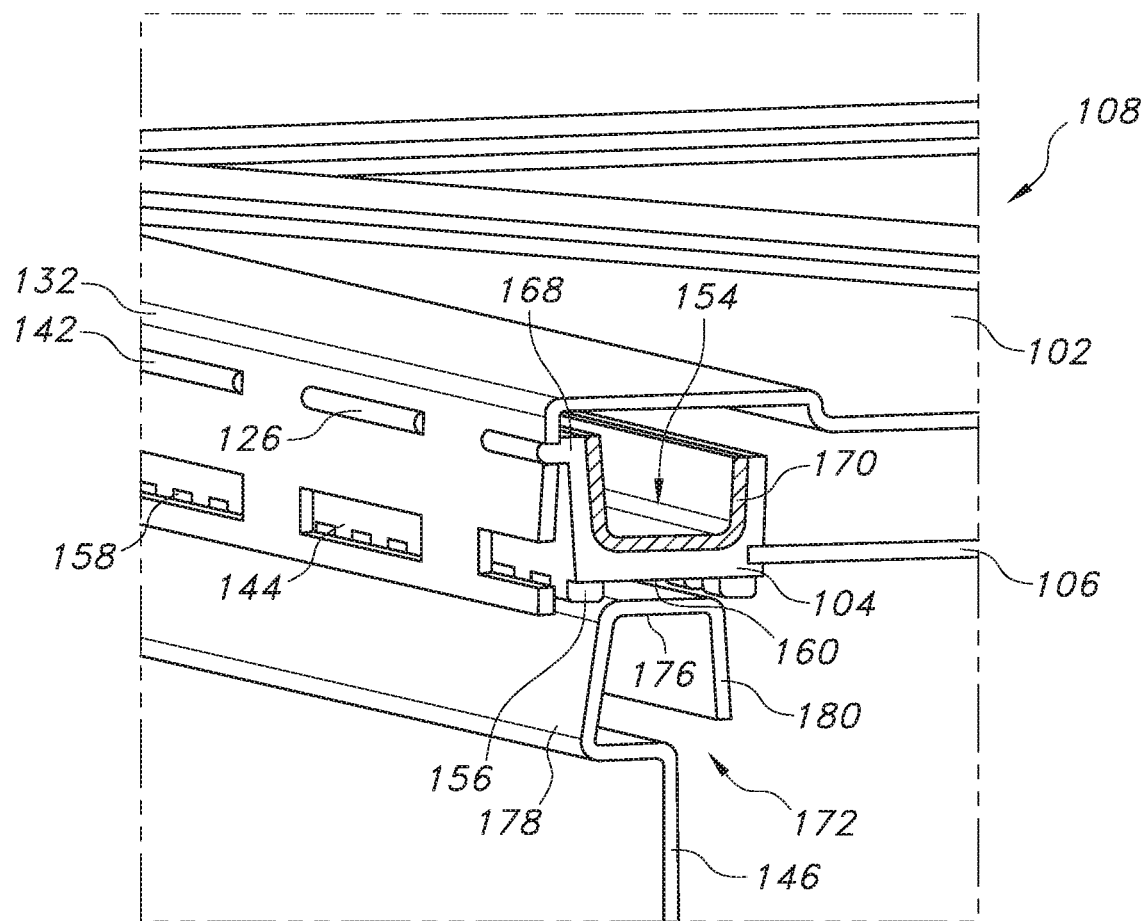
FIG. 11C provides yet another partial cross-section view of the sterilization packaging system of FIG. 10 when the sealing assembly is improperly installed.

FIG. 11A provides another partial cross-section view of the sterilization packaging system of FIG. 10 when the sealing assembly 108 is properly installed. As shown in FIG. 11A, the visual indicators 126 are visible and are shown to protrude from the lower openings 144 in the lip 132 of the lid 102, and the gasket 104 is secured in place and in contact with the seal rim 172. On the other hand, FIGS. 11B and 11C show that the visual indicators 126 do not protrude from the lower openings 144 in the lip 132 of the lid 102 when the sealing assembly 108 is not properly installed. Specifically, in FIG. 11B, the visual indicator 126 is misaligned and does not protrude from the lower openings 144 in the lip 132 of the lid. Instead, the seal rim 172 is not properly inserted into the recess 154 of the gasket 104, leaving a gap between the upper horizontal flange 176 and the upper surface 160 of the gasket 104 so that the visual indicator 126 is not able to protrude from the lower openings 144 in the lip 132 of the lid 102. A user would be alerted to such improperly closing of the lid upon inspection of the sealing assembly 108, where the protrusions 156 and indentations 158 are visible from the lower openings 144 and the visual indicator 126 does not protrude from the lower openings 144. Meanwhile, in FIG. 11C, the sealing assembly 108 is installed upside-down such that the seal rim 172 does not fit into the recess 154 of the gasket 104. Instead, the upper horizontal flange 176 of the seal rim 172 is in contact with the protrusions 156 on the upper surface 160 of the gasket 104 and the lid 102 is not able to properly close. A user would be alerted to such improperly closing of the lid upon inspection of the sealing assembly 108, where the protrusions 156 and indentations 158 are visible from the lower openings 144 and the visual indicator 126 does not protrude from the lower openings 144.

Figure 12:
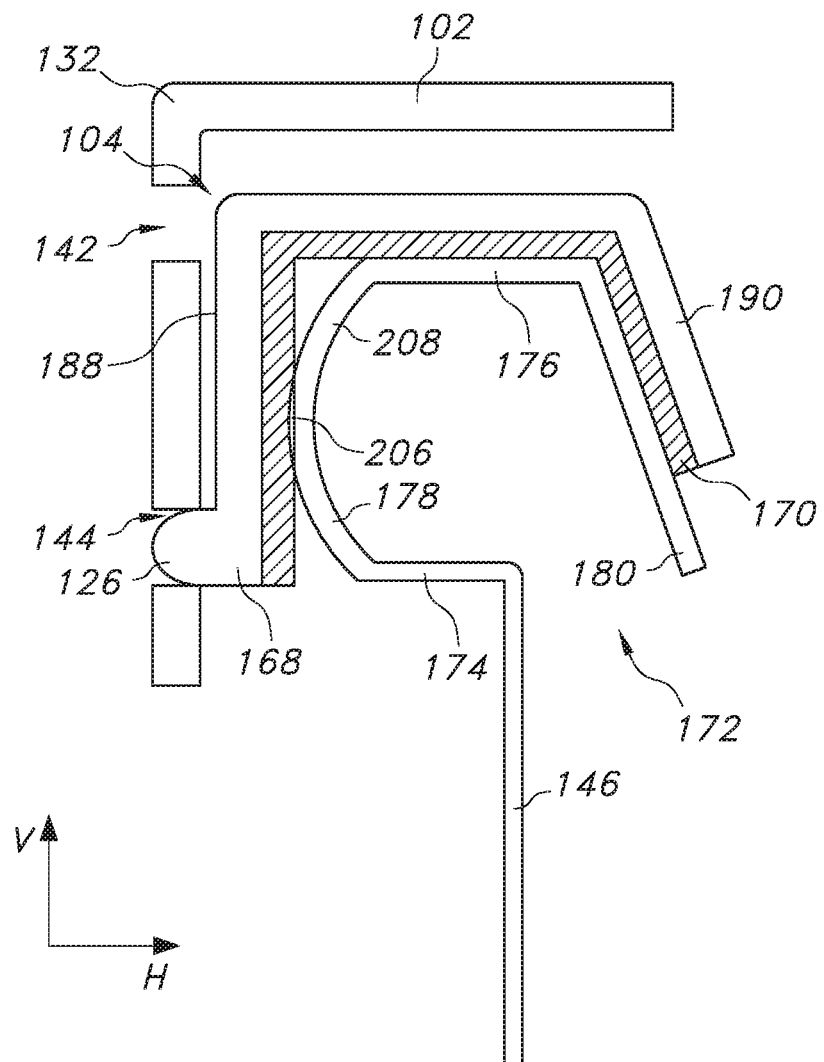
FIG. 12 provides a partial cross-section view of the sterilization packaging system according to another exemplary embodiment of the present invention.

Referring now to FIG. 12, a partial cross-section view of a sterilization packaging system according to another exemplary embodiment of the present invention is shown. Specifically, the seal rim 172 contains certain geometry to ensure that the visual indicator 126 can protrude through the lower opening 144 in the lip 132 of the lid 102 when the one-piece sealing assembly 108 is adequately sealed and correctly installed. For instance, the outer vertical flange 178 that extends in the vertical direction V can have a curved section 208 where the curved section 208 includes an area of compression 206 formed at a point of tangency with the gasket 104 (e.g., the second gasket material 170), where the deflection movement of the gasket 104 including the indicator 126 relative to the outer vertical flange 178 facilitates the indicator 126 to protrude from the lower opening 144. In this manner, the position of the outer vertical flange 178 encourages the compression of the optional second gasket material 170 and the proper placement of the outer edge 188 of the gasket 104 so that the visual indicator 126 can protrude through the lower openings 144 in the lip 132 of the lid 102, which signals to the user that the gasket 102 is properly sealed between the seal rim 172 and the lid 102.

Figure 13:
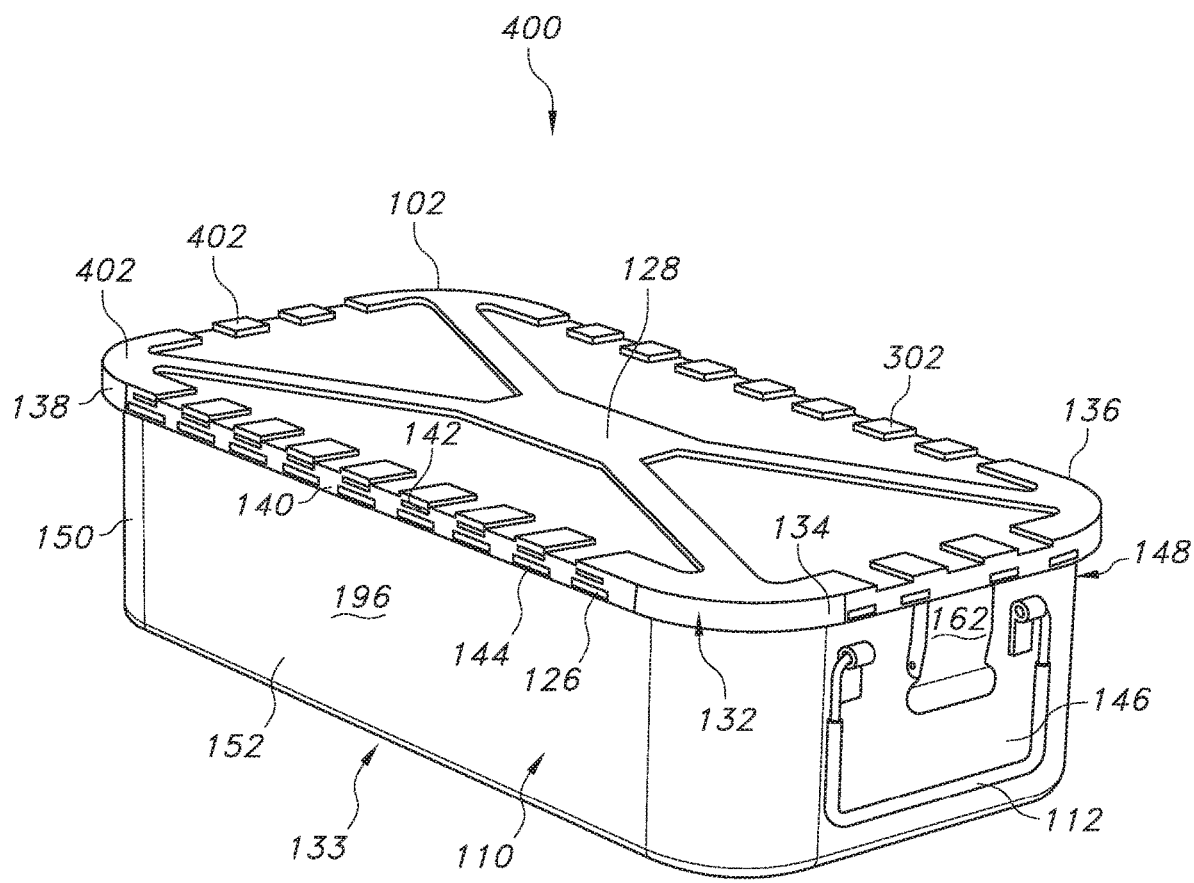
FIG. 13 provides a perspective view of a sterilization packaging system according to another exemplary embodiment of the present invention.

Referring now to FIG. 13, in another embodiment, the present invention is directed to sterilization packaging systems with features for sealing a volume against an ingress of contaminants are provided. Such features include a sealing assembly that includes a gasket and a sheet of filter material, where the sealing assembly seals a lid to a seal rim of a base. The gasket has an upper surface, an outer edge, and an inner edge, wherein the upper surface of the gasket is smooth and an upper surface of the lid includes a plurality of protrusions, wherein a channel is defined by the upper surface of the gasket and each of the plurality of protrusions. The sheet of filter material extends from an inner edge of the gasket, where the gasket completely surrounds the sheet of filter material. Further, each channel defined by the upper surface of the gasket and each of the plurality of protrusions facilitates the delivery of sterilization agent through the sheet of filter material when the sterilization packaging system is sealed with the sealing assembly.

Figure 14:
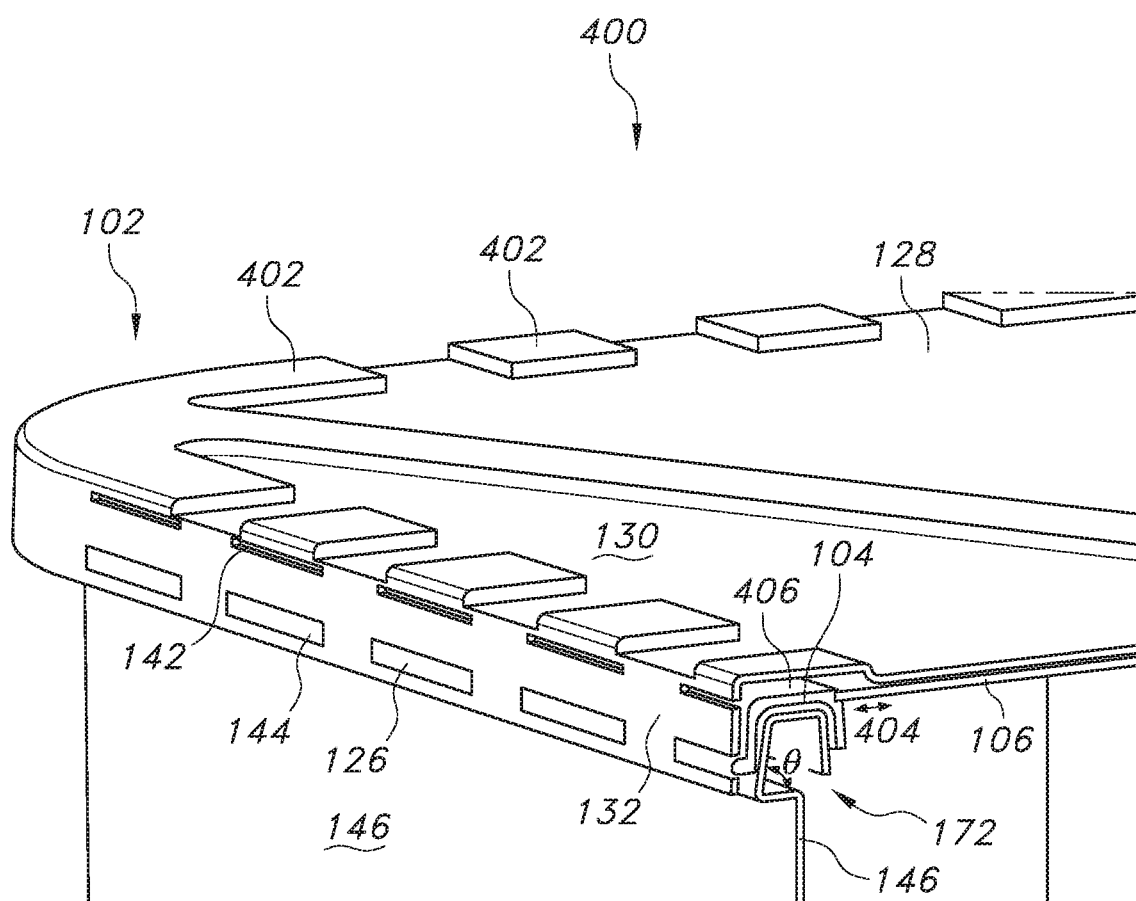
FIG. 14 provides a partial cross-section view of the sterilization packaging system of FIG. 13.
Figure 15:
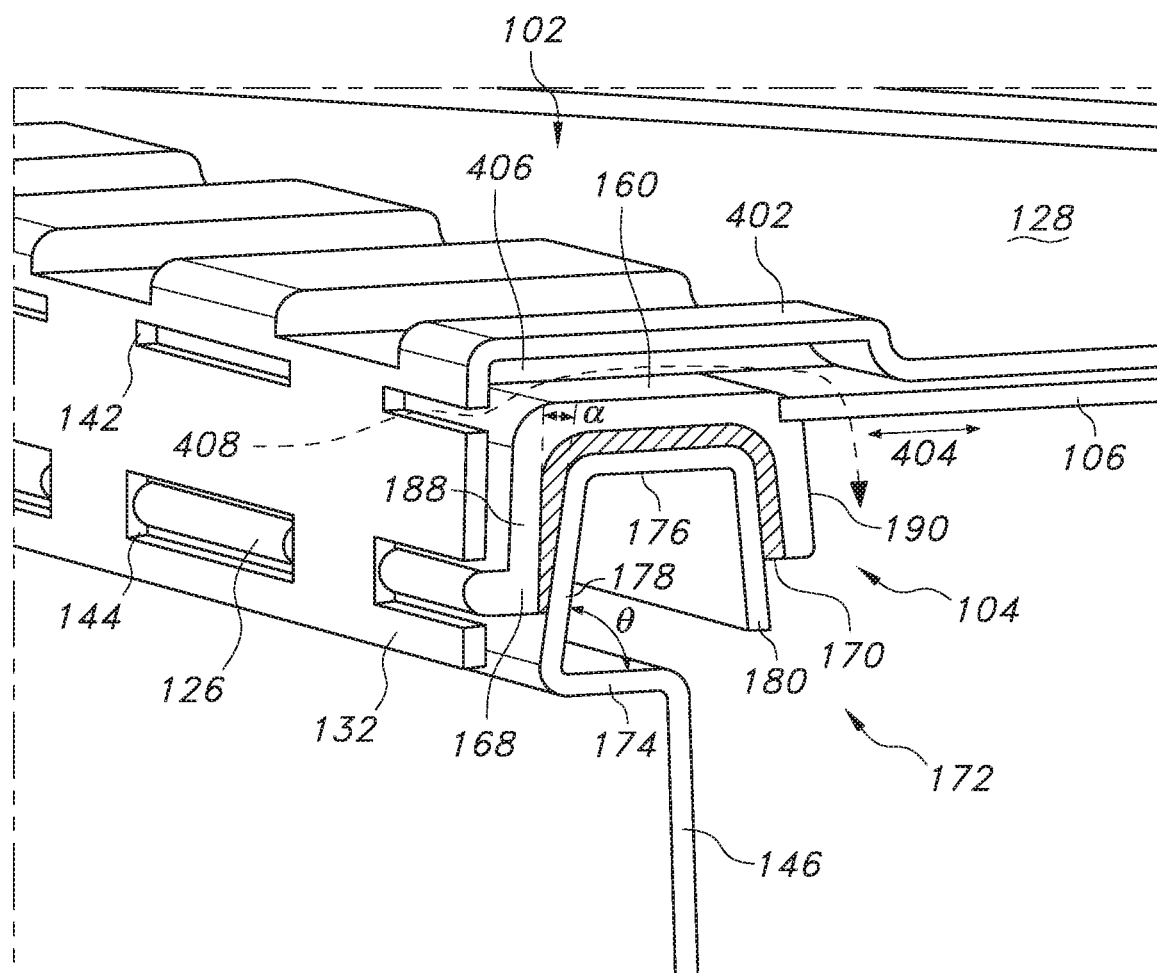
FIG. 15 provides another partial cross-section view of the sterilization packaging system of FIG. 13.

Specifically, FIG. 13 provides a perspective view of a sterilization packaging system according to an exemplary embodiment of the present subject matter. In the depicted embodiment, sterilization packaging system 400 includes a lid 102 and a base 110 defining a volume 196 for containing one or more items to be sterilized. The base 110 includes a lower surface 133, a first sidewall 146, a second sidewall 148, a third sidewall 150, and a fourth side wall 152 extending from the lower surface 133, where one or more handles 112 can be present on one or more of the sidewalls, although FIG. 1 shows a handle 112 present on the first sidewall 146. Referring to FIG. 7, which shows the base 110 without the lid 102 attached thereto, the first sidewall 146, the second sidewall 148, the third sidewall 150, and the fourth side wall 152 terminate at a seal rim 172 defining a perimeter 129. The various features of the seal rim 172 and how the seal rim 172 cooperates with the lid 102 to create a seal are shown in FIGS. 14 through 15 and are discussed in more detail below. The base 110 also includes an opening 131 to provide access to the volume 196 in which items to be sterilized can be placed.

Referring again to FIG. 13, the lid 102 includes an upper surface 128 defining a perimeter 128, where a lip 132 extends downward therefrom towards the base 110. The lip 132 includes a plurality of upper openings 142 and a plurality of lower openings 144 that can be positioned along a first side 134, a second side 136, a third side 138, and a fourth side 140 of the lip. The upper openings 142 facilitate the introduction of any suitable type of sterilization agent (e.g., steam, ethylene oxide, or hydrogen peroxide plasma) into the opening 131 in the base 110 as discussed in more detail below with respect to FIGS. 14 and 15. Meanwhile, the lower openings 144 can expose a visual indicator 126 when the lid 102 is adequately and properly sealed to the base 110 via a latch 162 that serves to engage and compress a sealing assembly between the lid 102 and the base 110. The base 110 and the lid 102 can be reusable and can be formed from a rigid material such stainless steel, anodized aluminum, polyetheretherketone (PEEK), polyaryletherketone, polyphenylsulphone (PPSU), polysulphone (PSU), filled PPSU, and filled PSU. Once sealed, the sealed sterilization packaging system 400 can then be transferred to sterilizing equipment and exposed to sterilization conditions as generally known in the art. Such sterilization conditions can include, for example, steam, ethylene oxide, or hydrogen peroxide plasma sterilization conditions. Sterilization conditions are the conditions present during a particular sterilization methodology utilized that substantially kills or completely destroys bacteria and other infectious organisms in an industrial or medical product to the desirable sterility assurance level (e.g., ≥10-6 log reduction for terminal sterilization).

As with the embodiment shown in FIG. 1, the sterilization packaging system 400 of FIG. 13 can include a sealing assembly 108, as shown in FIG. 2. In particular, the lid 102 is sealed to the base 110 via a one-piece sealing assembly 108 that is engaged and compressed via latch 162. The sealing assembly 108 can be disposable and seals the base 110 from the ingress of contaminants such as, e.g., bacteria and other infection causing materials or their vehicles. As shown in FIG. 2, the sealing assembly 108 includes a gasket 104 and a sheet of filter material 106. The gasket 104 completely surrounds the sheet of filter material 106. However, unlike the sterilization packaging system 100, the system 400 includes a gasket 104 that is free of indentations and protrusions on its upper surface 160. Instead, the upper surface 160 is smooth, while the lid 102 includes protrusions 402 that create a channel 406 to facilitate the delivery of sterilization agent 124 (e.g., steam, ethylene oxide, hydrogen peroxide plasma, etc.) into the base 110 of the sterilization packaging system via the sheet of filter material 106 to sterilize the contents contained within the volume 196 of the base 110.

Referring now to FIGS. 14-15, partial cross-section views of the sterilization packaging system 400 are shown. Specifically, the seal rim 172 contains certain geometry to ensure that the visual indicator 126 can protrude through the lower opening 144 in the lip 132 of the lid 102 when the one-piece sealing assembly 108 is adequately sealed and correctly installed. For instance, an angle θ can be formed between the outer vertical flange 178 that extends in the vertical direction V and the lower horizontal flange 174 that extends in the horizontal direction that is offset slightly from the vertical direction or axis V. For instance, the angle formed between the outer vertical flange 178 and the lower horizontal flange can range from about 65° to about 90°, such as from about 70° to about 85°, such as from about 75° to about 80°. Likewise, the angle α formed between the outer edge 188 of the gasket 104 and the outer vertical flange 178 can range from about 0° to about 25° C., Such as from about 5° to about 20°, such as from about 10° to about 15°, where the deflection movement of the gasket 104 including the indicator 126 relative to the outer vertical flange 178 facilitates the indicator 126 to protrude from the lower opening 144. In this manner, the position of the outer vertical flange 178 encourages the compression of an optional second gasket material 170 and the proper placement of the outer edge 188 of the gasket 104 so that the visual indicator 126 can protrude through the lower openings 144 in the lip 132 of the lid 102, which signals to the user that the gasket 102 is properly sealed between the seal rim 172 and the lid 102.

In addition, as also shown in FIGS. 13-15, the protrusions 402 present on the upper surface 128 of the lid 102 in conjunction with the smooth upper surface 160 of the gasket 104 define channels 406 to facilitate the delivery of a sterilization agent 408 through the upper openings 144 on the lip 132 of the lid 102 through the channels 406 and ultimately to the sheet of filter material 106 so that the contents of the sterilization packaging system 400 can be sterilized. Further, the protrusions 402 can extend an overhang distance 404 past the inner edge 190 of the gasket 104 to ensure that the sterilization agent 408 can reach the sheet of filter material 106.

Further, it is to be understood that although not repeated in detail with respect to FIGS. 13-15, any of the various features described above with respect to FIGS. 1-12 and sterilization packaging systems 100 and 300 may also be incorporated into the sterilization packaging system 400 to the extent that such features do not conflict with the features required by sterilization packaging system 400.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization packaging system having a volume for containing items to be sterilized, the sterilization packaging system comprising:
a lid having an upper surface defining a perimeter and a lip extending downward from the perimeter, wherein the lip includes a plurality of upper openings and a plurality of lower openings;
a base having a lower surface, a first sidewall, a second sidewall, a third sidewall, and a fourth side wall extending from the lower surface, wherein the first sidewall, the second sidewall, the third sidewall, and the fourth sidewall terminate at a seal rim defining a perimeter; and
a sealing assembly, wherein the sealing assembly seals the lid to the seal rim of the base, the sealing assembly comprising:
a gasket having an upper surface, an outer edge, and an inner edge, wherein the upper surface of the gasket comprises a first row of alternating protrusions and indentations and a second row of alternating protrusions and indentations that define a channel therebetween,
a sheet of filter material extending from an inner edge of the gasket, wherein the gasket completely surrounds and partially overlaps the sheet of filter material, wherein the indentations and channel facilitate the delivery of sterilization agent through the sheet of filter material when the sterilization packaging system is sealed with the sealing assembly.

2. The sterilization packaging system of claim 1, wherein a visual indicator is present on the outer edge of the gasket.

3. The sterilization packaging system of claim 2, wherein the visual indicator is visible from the lower openings in the lip when the sterilization packaging system is adequately sealed by the sealing assembly.

4. The sterilization packaging system of claim 2, wherein the visual indicator protrudes from the lower openings in the lip when the sterilization packaging system is adequately sealed by the sealing assembly.

5. The sterilization packaging system of claim 1, wherein the seal rim comprises an upper horizontal flange, wherein the upper surface of the gasket, the outer edge of the gasket, and the inner edge of the gasket define a recess for receiving the upper horizontal flange.

6. The sterilization packaging system of claim 1, wherein the gasket comprises a first gasket material and a second gasket material.

7. The sterilization packaging system of claim 6, wherein the first gasket material is less compressible and more rigid than the second gasket material.

8. The sterilization packaging system of claim 6, wherein the inner edge of the gasket is defined by the first filter material.

9. The sterilization packaging system of claim 6, wherein the first gasket material comprises a rigid polymer and the second gasket material comprises a foam.

10. The sterilization packaging system of claim 1, wherein the sheet of filter material is corrugated.

11. The sterilization packaging system of claim 1, wherein the sheet of filter material extends in a longitudinal direction and a transverse direction, wherein one or more longitudinal support members is disposed on a surface of the sheet of filter material in the longitudinal direction and one or more transverse support members is disposed on the surface of the sheet of filter material in the transverse direction.

12. The sterilization packaging system of claim 1, wherein the sealing assembly provides a continuous sealing interface between the lid and the base of the sterilization packaging system.

13. The sterilization packaging system of claim 1, wherein the sealing assembly is disposable.

14. The sterilization packaging system of claim 1, wherein the lid and the base are reusable.

15. The sterilization packaging system of claim 1, wherein the gasket includes a pair of interior facing opposing tabs.

16. The sterilization packaging system of claim 1, wherein the seal rim comprises an outer vertical flange and a lower horizontal flange, wherein an angle formed between the outer vertical flange and the lower horizontal flange ranges from about 65° to about 90°.

17. The sterilization packaging system of claim 1, wherein the seal rim comprises an outer vertical flange and a lower horizontal flange, wherein the outer vertical flange includes a curved section having an area of compression that forms a point of tangency with the gasket.

* * * * *